United States Patent [19]
Boyle

[11] Patent Number: 4,976,717
[45] Date of Patent: Dec. 11, 1990

[54] UTERINE RETRACTOR FOR AN ABDOMINAL HYSTERECTOMY AND METHOD OF ITS USE

[76] Inventor: Gary C. Boyle, Rte. 2, Box 14-A, Blountville, Tenn. 37617

[21] Appl. No.: 342,123

[22] Filed: Apr. 24, 1989

[51] Int. Cl.$^5$ .............................................. A61B 17/00
[52] U.S. Cl. ....................................... 606/119; 604/55
[58] Field of Search ............... 606/119, 121, 122, 135, 606/160; 604/55, 170; 128/749, 751–754, 20

[56] References Cited

U.S. PATENT DOCUMENTS

| | | | |
|---|---|---|---|
| 2,400,251 | 5/1946 | Nagel | 606/119 |
| 3,777,743 | 11/1973 | Binard et al. | 606/119 X |
| 3,809,091 | 5/1974 | Shute | 606/119 X |
| 4,000,743 | 1/1977 | Weaver | 606/119 |
| 4,430,076 | 2/1984 | Harris | 606/119 X |
| 4,606,336 | 8/1986 | Zeluff | 604/55 X |

FOREIGN PATENT DOCUMENTS 0319394 6/1989 European Pat. Off. ............ 606/119

*Primary Examiner*—Mickey Yu
*Assistant Examiner*—Kerry Owens
*Attorney, Agent, or Firm*—Luedeka, Hodges, & Neely

[57] ABSTRACT

A uterine retractor for an abdominal hysterectomy includes elongate shaft means having first and second opposite ends, piercing means located on the first end of the shaft means for piercing through the fundus of the uterus, and engagement means located on the second end for engaging the cervix. In use, the first end of the shaft means is guided up through the vaginal canal and inserted into the interior space of the uterus through the cervical canal. The retractor is then urged forwardly to cause the piercing means to pierce through the fundus of the uterus to position the first end of the shaft means outside the uterus in the abdominal cavity. The projecting first end of the shaft means is accessed through an incision formed in the lower abdominal wall, whereupon the retractor is pulled through the interior space of the uterus until the engagement means engages the cervix. In this position, the retractor is used to move the cervix to a desired position facilitating separation of the uterus from attached body structure including the vagina. After the uterus is separated, the retractor may be used to lift the uterus out of the abdominal cavity through the incision.

12 Claims, 2 Drawing Sheets

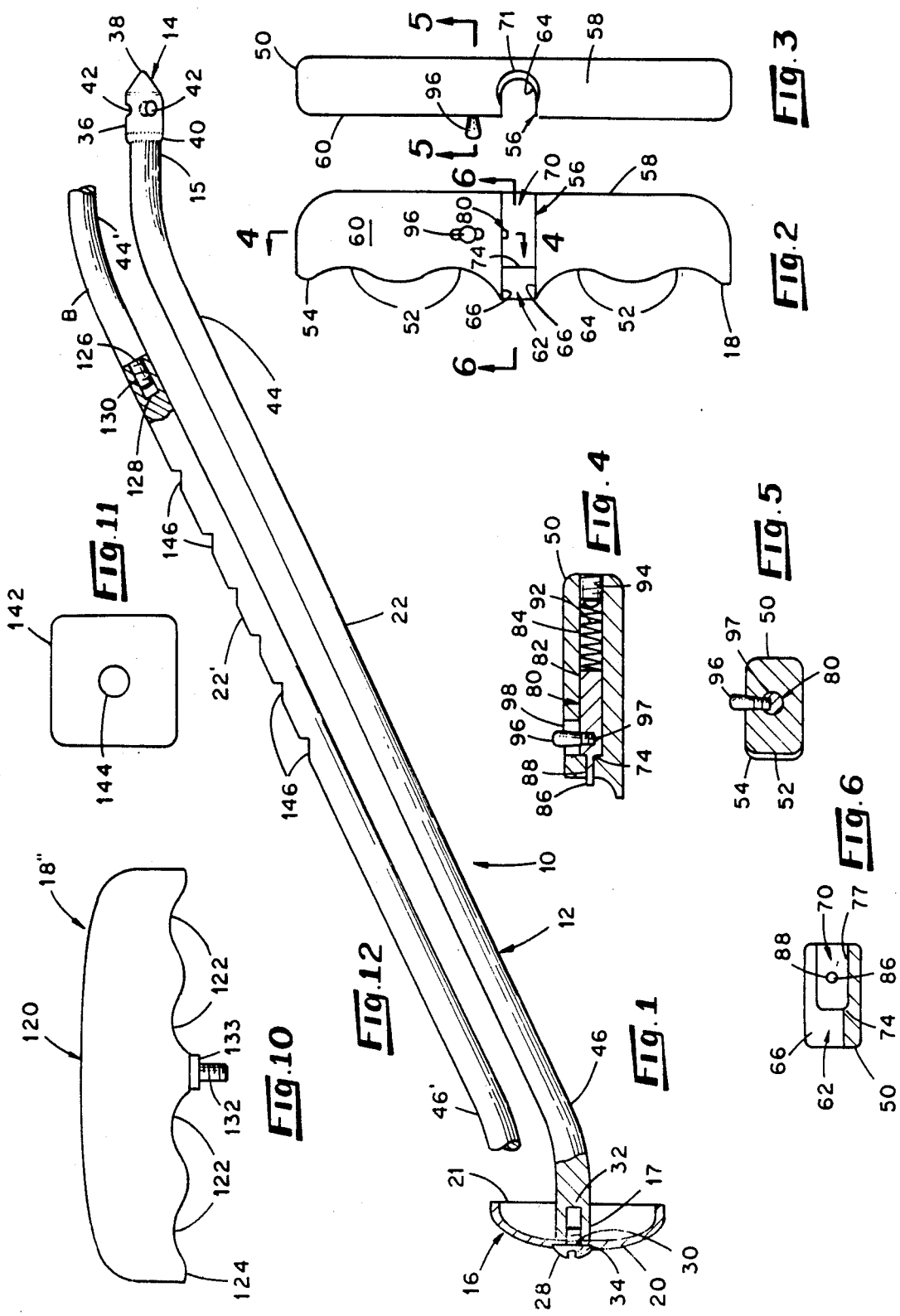

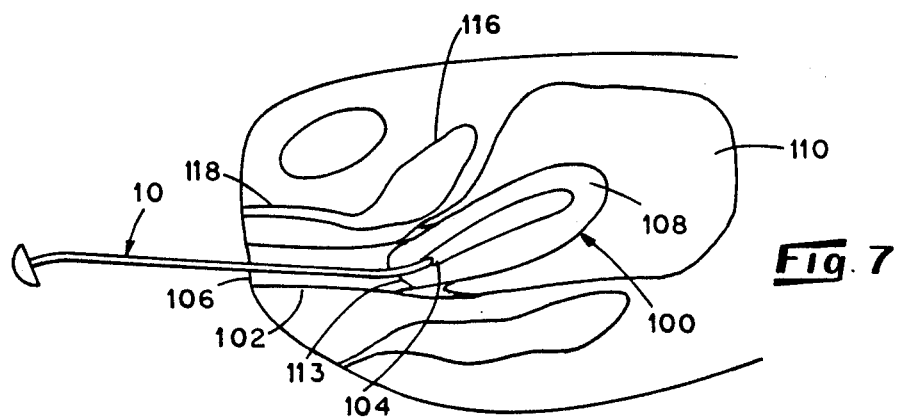
_Fig. 7_
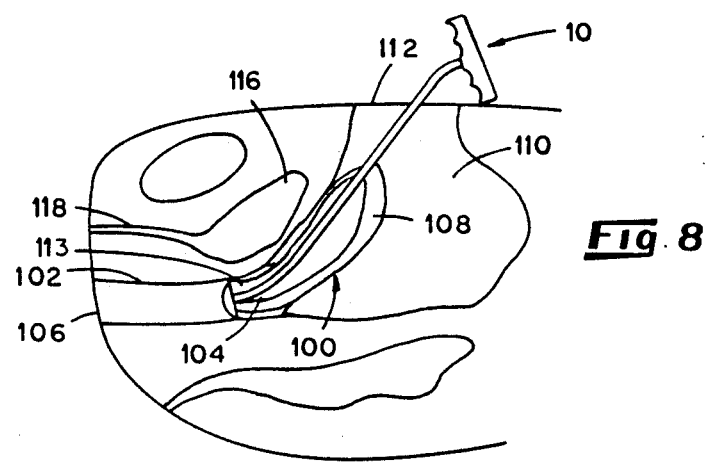
_Fig. 8_
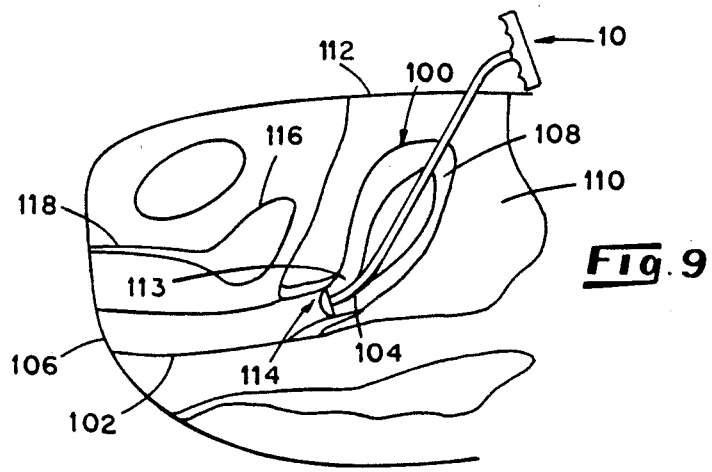
_Fig. 9_

UTERINE RETRACTOR FOR AN ABDOMINAL HYSTERECTOMY AND METHOD OF ITS USE

The present invention relates to surgical instruments and methods for performing hysterectomies and related procedures, and more particularly relates to a uterine retractor for an abdominal hysterectomy and a method of its use.

In an abdominal hysterectomy procedure, the uterus and often the adnexa are separated from their attachments in the abdominal cavity, and removed through an incision made across and through the lower abdominal wall. The separation is performed at the base of the uterus adjacent the cervix in the anterior and posterior cul-de-sac regions where there is a very close arrangement of the uterus relative to critical adjacent structure, particularly the rectum, bladder and ureter. Because of this arrangement, considerable skill and careful attention are required on the part of the surgeon during the procedure to avoid undesired involvement or contact with the adjacent structure as access is gained to the various connective tissue and separation and reconstruction procedures are performed. The close arrangement of the base of the uterus relative to critical adjacent structure also makes it difficult to use modern adjunct surgical techniques such as stapling and lasering, for example, in abdominal hysterectomies.

The typical procedure for an abdominal hysterectomy involves traction of the uterus cranially in order to lessen the difficulties presented by the uterine arrangement. However, any traction o other movement that can be achieved using conventional surgical instruments and techniques is not particularly effective for this purpose.

Accordingly, it is an object of the present invention to provide a uterine retractor for an abdominal hysterectomy and a method of its use.

It is another object of the invention to provide a uterine retractor and method of the character described which minimizes the likelihood of undesirable involvement or contact with adjacent body structure.

A further object of the invention is the provision of a uterine retractor and method of the character described which reduces the time and effort required to perform an abdominal hysterectomy.

Still another object of the invention is to provide a uterine retractor and method of the character described which facilitates the use of staples, lasers and similar modern surgical tools and methods.

A further object of the invention is the provision of a uterine retractor for performing an abdominal hysterectomy which is simple in construction and which is relatively easy to use.

The foregoing and other objects and advantages of the present invention may be further understood with reference to the following detailed description of preferred embodiments when considered in conjunction with the accompanying drawings in which:

FIG. 1 is a side view, partially in section, illustrating features of a shaft portion of a uterine retractor constructed in accordance with the present invention;

FIG. 2 is a side elevational view illustrating features of a handle for attachment to the shaft portion of the uterine retractor shown in FIG. 1;

FIG. 3 is an end elevational view of the handle shown in FIG. 2 from the right-hand side thereof;

FIG. 4 is a view taken along line 4—4 of the handle shown in FIG. 2;

FIG. 5 is a view taken along line 5—5 of the handle shown in FIG. 3;

FIG. 6 is a view taken along line 6—6 of the handle shown in FIG. 2;

FIGS. 7 through 9 are schematic views illustrating aspects of a method of performing an abdominal hysterectomy using a retractor constructed in accordance with the invention;

FIG. 10 is a side view illustrating features of another form of the handle shown in FIG. 2;

FIG. 11 is a front elevational view of a uterine retainer for use in a retractor of the invention; and FIG. 12 is a fragmentary side view, partially in section, illustrating features of another form of the shaft shown in FIG. 1 and adapted for use with the handle and retainer shown in FIGS. 10 and 11, respectively.

In general, the present invention includes a uterine retractor for use in performing an abdominal hysterectomy which involves removal of the uterus through an abdominal incision, the uterus having a cervix at one end connected to the vagina with a cervical canal opening into the vaginal canal and through which access is gained to the interior space of the uterus from the vaginal canal, and a fundus closing the other end of the uterus and located out in the abdominal cavity. The retractor comprises elongate shaft means having first and second opposite ends. Piercing means are located adjacent the first end of the shaft means for being guided into the interior space of the uterus through the cervical canal from the vaginal canal, and are configured to pierce through the fundus of the uterus to position the first end of the shaft means outside the uterus in the abdominal cavity. The retractor further comprises engagement means located adjacent the second end for engaging the cervix and configured to engage the cervix and apply a force to the cervix to facilitate movement of the cervix to desired positions in response to application of a force on the retractor from the first end positioned outside the uterus in the abdominal cavity.

The retractor is used to perform an abdominal hysterectomy by inserting the first end of the shaft means into the vaginal orifice, guiding the first end up through the vaginal canal, and inserting the first end into the interior space of the uterus through the cervical canal. The piercing means is then employed to pierce through the fundus of the uterus so that the first end projects out into the abdominal cavity. Access is gained to the projecting first end through the abdominal incision, and a force is applied to the cervical engagement means from the projecting first end to cause the engagement means to engage and move the cervix to a desired position to facilitate separation of the uterus from adjacent attached body structure, including the vagina. This is preferably accomplished by gripping and pulling the first end of the retractor cranially, which in turn pulls the cervix and the base of the uterus cranially so that the vagina is stretched out, giving the surgeon easy access to the area of intersection between the uterus and the vagina where the separation is typically performed. With the vagina thusly stretched, it will be appreciated that the uterus may be separated from the vagina at a location that is spaced away from the bladder, ureter and other important adjacent structure, reducing the likelihood of any undesired involvement or contact therewith during the procedure.

In a preferred embodiment, the retractor further includes handle means attachable to the first end of the shaft means. The handle means are configured to facilitate the application of a force on the engagement means from the first end and thus facilitate movement of the cervix to desired positions.

A retractor 10 constructed in accordance with a preferred embodiment of the invention will now be described with reference to FIGS. 1 through 6. The retractor 10 includes as its main components elongate shaft means generally designated at 12, piercing means generally designated at 14 and located adjacent a first end 15 of shaft means 12 for piercing through the fundus of the uterus, and engagement means generally designated at 16 and located adjacent a second end 17 of shaft means 12 for engaging the cervix.

In a preferred embodiment, the retractor 10 also includes handle means indicated generally at 18 (FIGS. 2 through 6) which are attachable to shaft means 12 on the first end 15 adjacent piercing means 14 as described more fully hereinafter.

Engagement means 16 are preferably provided by a pessary cup 20 which is attached to the second end 17 of shaft means 12 in a manner to be described, and which is arranged so that it opens generally toward the first end 15. The cup 20 is shaped to fit in a surrounding or mating fashion over the outer protruding conical surface of the cervix to facilitate the exertion of a controlled force on the cervix and thus the uterus, as will be described. The cup 20 has a circumferentially extending outer lip 21 which is spaced radially from the cup sufficient to cause the lip to extend to near the anterior and posterior uteri fornices so that the cup fully covers the outer surface of the cervix.

Shaft means 12 are preferably provided by a solid elongate, cylindrical rod 22 having first and second opposite ends corresponding to the first and second ends 15 and 17 of the shaft means, respectively, and referred to hereinafter as such. The first end 15 of the rod 22 is associated with piercing means 16 and handle means 18, and the second end 17 is associated with the cup 20. The diameter of the rod 22 is preferably uniform along its length.

The pessary cup 20 is preferably attached to the second end 17 of the rod 22 using a screw 28 which is received through an opening 30 provided in the center of the cup. The screw 20 is threadably received into a blind bore 32 provided in the second end 17. The head of the screw 28 may rest in a flat recess 34 provided on the outer surface of the cup 20 surrounding the opening 30.

Piercing means 14 are preferably provided by an elongate cylindrical formation 36 which is formed on the first end 15 of the rod 22 as an integral part thereof coaxially relative to the immediately adjacent length of the rod. Along at least a major portion of its length, the cylindrical formation 36 preferably has a diameter slightly greater than that of the rod 22 and the formation 36 tapers forwardly to a pointed tip 38 which is used to pierce through the fundus of the uterus as will be described. A neck 40 provides the transition between the rod 22 and the larger diameter cylindrical formation 36, the latter extending forwardly from the neck 40 with a substantially uniform diameter until it begins to taper toward the tip 38.

A plurality of circumferentially spaced apart recesses 42 are disposed on the surface of the formation 36. Preferably, four equally spaced-apart recesses 42 are provided around the formation 36. The recesses 42 are arranged in a plane that is disposed substantially perpendicular to the axis of the formation 36 approximately midway along the length of the formation, and are preferably in the nature of hemispherical indentations. As described below, the recesses 42 facilitate attachment of handle means 18 to the rod 22 and the spacing of the recesses 42 about the circumference of the formation 36 enables the handle means to be rotated and locked into desired positions.

A pair of bends 44 and 46 are provided in the rod 22 and are associated with the first and second ends 15 and 17 of the rod, respectively. The bend 46 is spaced from the second end 17 of the rod 22 by a distance of about 1 inch, which is the average length of a cervical canal. The bend 44 associated with the first end 15 of the rod 20 is spaced from the formation 36 approximately the same distance. The cup 20 is disposed so that a plane containing the lip 21 is substantially perpendicular to the portion of the rod 22 extending outwardly from bend 46 toward the second end 17.

The rod 22 is preferably substantially straight along its length between the bends 44 and 46. Preferably, the diameter of the rod is about ¼ inch and the overall length of the rod is about 12 inches.

In the illustrated embodiment, the bends 44 and 46 dispose the straight portions of the rod 22 extending outwardly therefrom along lines which intersect the midlength axis of the rod at a substantially equal bend angle which is preferably less than about 30°, and most preferably about 25°. The bend angle is selected to correspond generally to the average or expected angle between the cervical canal and the remaining portion of the uterus extending out therefrom into the abdominal cavity. As will be described, this facilitates placement of the retractor 10 into the uterus, and correct positioning of the cup 20 over the cervix.

It is preferred that the straight portions of the rod 22 extending out from the bends 44 and 46 be disposed along substantially parallel lines. As a result, the longitudinal axis of the cylindrical formation 36 is substantially perpendicular to the plane of the lip 21 of the cup 20. Thus, when the rod 22 is rotated about its midlength axis, say 180°, the plane of the lip 21 is shifted in space by an angle that is twice that of the bend angle when the cup 20 is viewed parallel to the plane. This facilitates positioning of the cup 20 relative to the cervix in an advantageous supporting contact relationship during use of the retractor 10 in performing a hysterectomy.

With reference now to FIGS. 2 through 6, handle means 18 are preferably provided by an elongate rectangular grip 50 having four closely adjacent curvilinear finger holds 52 provided along a front edge 54. The dimensions of the grip 50 and the configuration of the finger holds 52 enable the grip to be held comfortably and securely by wrapping the hand around the grip along a grip axis oriented generally parallel to the length of the grip with the fingers supported in the finger holds, and with the palm against a back edge 55 of the grip extending generally parallel to the front edge 54.

A channel 56 extends across the grip 50 between the front and back edges 54 and 55 substantially perpendicular to the length of the grip. The channel 56 opens on its ends adjacent the front and back edges 54 and 55, and openly communicates along its length with a generally flat face 60 of the grip 50. As will be described, the formation 36 and a short portion of the rod 22 adjacent the formation are received in the channel 56 to facilitate attachment of the grip 50 to the rod.

A first segment 62 of the channel 56 extends inwardly from the front edge 54 of the grip 50 and has a bottom portion 64 with a semicircular cross-section. Substantially parallel sidewalls 66 of the first segment 62 extend up to the face 60 of the grip 50 substantially tangentially from the bottom 64. The diameter of the semicircular bottom 64 is about, but slightly greater than, the diameter of the rod 22. It will be appreciated that the portion of the rod 22 adjacent the neck 40 will therefore fit down into the channel 56 in the first segment 62 thereof.

A second segment 70 of the channel 56 extends between the first segment 62 and the back edge 55 of the grip 50. The second segment 70 has a bottom portion 71 with a somewhat less than full circular cross section. The diameter of the bottom 71 of the second segment 70 is greater than that of the semi-circular bottom 64 of the first segment 62, as best seen in FIG. 3. In addition, the diameter of the bottom 71 of the second segment 70 is about, but slightly greater than, the diameter of the cylindrical formation 36 located on the first end 15 of the rod 22. The length of the second segment 70 is approximately equal to the length of the formation 36.

The first and second segments 62 and 70 of the channel 56 are coaxial, consistent with the coaxial arrangement of the cylindrical formation 36 relative to the portion of the rod 22 adjacent the neck 40. A shoulder 74 provides the transition between the first and second segments 62 and 70 of the channel 56.

The flat sidewalls 66 of the first segment 62 also form the sidewalls of the second segment 70 so that the opening of the channel 56 along the face 60 has a uniform width, as can be seen in FIG. 2. However, the width of the opening of the channel 56 along the face 60 as defined by the sidewalls 66 is less than the diameter of the formation 36 located on the first end 15 of the rod 22.

It will thus be recognized that the second segment 70 of the channel 56 expands out into the body of the grip 50 at a location spaced beneath the face 60, since the diameter of the bottom 71 of the second segment 70 is greater than the width between the sidewalls 66. Thus, the formation 36, which has a diameter greater than the width between the sidewalls 66 but slightly less than the diameter of the bottom 71, may be inserted longitudinally into the segment 70 from the end of the channel 56 opening to the back edge 55. The formation 36 will, however, be restricted against any non-longitudinal movement, particularly movement out of the opening of the channel adjacent the face 60.

The formation 36 on the first end 15 of the rod 22 may be positioned in the second segment 70 of the channel 56 by placing the straight portion of the rod extending between the formation 36 and the bend 46 down into the channel 56 with the plane containing the bend 46 approximately perpendicular to the length of the grip 50. At this point, the position of the rod 22 is such that the formation 36 is located back of the back edge 58 of the grip 50 since the diameter of the formation 36 is greater than the width across the opening of the channel 56 and thus cannot be placed directly down into the channel from the face 60. Then, the rod 22 is slid longitudinally along the channel 56 toward the front edge 54 drawing formation 36 into the second segment 70 of the channel until the neck 40 engages the shoulder 74.

The grip 50 is attached to the formation 36 on the rod 22 by means of a sliding pin 80 that projects out into second segment 70 of the channel 56, and which is received into a selected one of the recesses 42 provided on the formation. The pin 80 is disposed along a line that intersects the longitudinal axis of the second segment 70 of the channel 56, which coincides substantially with the longitudinal axis of the formation 36 when the latter is placed therein as described above.

The pin 80 includes a main elongate cylindrical portion 82 that is slidably received in a bore 84 provided in the grip 50. The bore 84 is disposed parallel to the length of the grip 50 as shown in FIG. 4.

The pin 80 also includes a reduced diameter elongate cylindrical nose portion 86 that is projectable out into the second segment 70 of the recess 56 through an aperture 88 formed at the end of the bore 84 adjacent the channel 56. It is this nose portion 86 that is received into the recesses 42 of the formation to interengage the grip 50 and rod 22.

The aperture 88 has a diameter slightly greater than that of the nose portion 86 of the pin 80, but less than that of the larger diameter portion 82, so that a shoulder 90 of the pin 80 abuttingly engages the end of the bore 84. This limits longitudinal movement of the pin 80 in the lefthand direction as shown in FIG. 4 to a stopped position at which the nose portion 86 of the pin 80 extends out into the second segment 70 of the channel 56.

The length of the nose portion 86 extending through the aperture 88 and out into the channel 56 is sufficient to cause the nose to engagingly enter a selected one of the recesses 42 in the formation 36 when the pin 80 is in the stopped position and the formation is placed into the second portion 70 of the channel as aforesaid, so that the grip 50 and rod are interengaged.

The pin 80 is urged toward the end of the bore 84 to the stopped position by a spring 92 which is disposed in the bore 84 to exert opposing forces between the end of the pin 80 and a headless screw 94 threadably received in the opposite end of the bore 84 adjacent the top of the grip 50.

A knob 96 projects above the face 60 of the grip 50 through an oblong opening 98 provided therein in open communication with the bore 84. The lower end of the knob 96 is threadably received in an opening 97 provided in the top of the pin 80.

The configuration and position of the opening 98 along the bore 84 are such that the knob 96 may be employed through the action of a finger or thumb, for example, to push the pin 80 back in the bore 84 against the force of the spring 92 sufficient to withdraw the nose portion 86 from the channel 56 and thus facilitate insertion of the cylindrical formation 36 of the rod 22 into the channel 56 as described earlier. Alternately, the neck 40 adjacent the formation 36 may be used as an agency to cause the pin 80 to be resiliently urged back into the aperture 88 permitting movement of the formation 36 into the channel. This can be accomplished by forming the neck 40 so that it gradually slopes outwardly toward the formation and thus presents an inclined surface of engagement to the nose portion 86 of the pin when the formation is inserted into the channel as aforesaid. The nose portion 86 will thus slide up on the neck 40 as the formation advances into the channel which will urge the pin 80 back into the aperture 88.

Once the formation 36 has been inserted into the channel 36 and the rod 22 has been rotated to position a selected one of the recess 42 in alignment with the path of movement of the pin 80, the knob 96 may be released (if it is being held) and the force of the spring 92 will urge the pin 80 and thus the nose portion thereof 86 into the channel 56 causing the nose portion to enter the recess 42, locking the grip 50 into position on the rod 22. Alternately, the nose portion 86 of the pin 80 may be permitted to rest in engagement on the outer surface of the formation 36 under the influence of the spring 92. Then, when the rod 22 is rotated the nose 86 will slide on the surface of the formation 36 until a recess 42 is brought into alignment with the pin 80, at which time the spring 92 will urge the nose 86 into the recess 42 causing the grip 50 and rod 22 to become interengaged.

It is to be noted that the knob 96 may be manipulated as aforesaid moving the pin 80 out of the recesses 42 to enable the grip 50 to be disposed at a number of different positions about the cylindrical formation 36, the number of positions corresponding to the number of recesses provided on the formation 36. Thus, in the preferred embodiment in which four recesses 42 are provided and are spaced apart approximately 90° about the formation 36, the grip 50 may be locked into position on the shaft 22 at any one of four 90° spaced apart positions. In this regard, the recesses 42 are preferably positioned with two diametrically opposed recesses lying in the plane containing the bend 46 so that the grip 50 may be locked into position on the rod 22 with the length of the grip 50 disposed substantially parallel to the plane of the bend 46. The other two diametrically opposed recesses lie along a line that is generally perpendicular to the plane containing the bend 46.

Those of ordinary skill in the art will recognize that the instrument may be used in conjunction with conventional surgical procedures for abdominal hysterectomies. Thus, a lengthy description of such procedures including pre-op and post-op procedures; and the technical aspects of the surgery itself, are omitted herein for the purpose of brevity. There are, however, certain novel and advantageous aspects associated with the abdominal hysterectomy which is performed using the retractor 10 of the present invention and to assist in an understanding thereof the schematic illustrations of FIGS. 7 through 9 are provided showing portions of the procedure.

With initial reference to FIG. 7, the first end 15 of the retractor 10 is shown after having been positioned in the fold of the uterus 100, which is accomplished by guiding the first end up through the vaginal and cervical canals 102 and 104 from the vaginal orifice 106. The rod 22 has been rotated so that the first bend 44 generally follows the disposition of the uterus 100 inwardly of the cervical canal 104 causing the first end 15 of the rod to point generally toward the fundus 108 of the uterus.

From the position shown in FIG. 7, the retractor 10 is moved up through the fold of the uterus 100 until the tip 38 makes contact with the fundus 108. Then, the retractor 10 is urged lengthwise so that the tip 38 pierces through the fundus 108, causing the first end 15 and formation 36 to be positioned in the abdominal cavity 110.

Access is gained to the retractor 10 and abdominal cavity 110 through an abdominal incision 112. The grip 50 is attached to the rod 22 as has been described to facilitate the application of longitudinal and rotational forces to the rod 22, and particularly the pessary cup 20 located on the second end 17 of the rod. Upon attachment, for example, the grip 50 may first be used to draw the rod 22 through the uterus 100 and bring the cup 20 into engagement over the outer surface of the cervix 113 with the length of the rod extending out from the second bend 46 being located in the cervical canal 104 as shown in FIG. 8, and with the retractor rotated 180° so that the second bend 46 is positioned in substantial conformance to the disposition of the cervical canal 104. In this position, the retractor 10 may be used to apply forces on the cervix 113 and thus the uterus 104 to facilitate separation of the uterus from its bodily connections.

FIG. 9 illustrates one manner in which the retractor 10 may be used to position the uterus 100 advantageously for separation. As shown, the retractor 10 has been employed to apply a force to the cervix 113 to move the cervix and uterus 100 in the direction of the head (cranially) causing the flexible vaginal wall in the area of the vaginal vault 114 to be stretched or elongated accordingly.

This moves the base of the uterus 104 adjacent the vault 114 out of the relatively inaccessible cul-de-sac regions, exposing a substantial length of the vaginal wall where the uterus is connected to the vagina. The uterus 104 is also supported along its length on the rod 22 in an elevated or upright position against any tendency of the uterus to collapse upon itself, or to one side or the other.

With the uterus 104 thusly positioned, it will be appreciated that separation is made substantially less complicated since the base of the uterus is spaced from the adjacent body structure, particularly the bladder 116 and ureter 118, and is exposed to the surgeon in an area of relatively easy access. Also, because the base of the uterus is exposed in an area of relatively easy access, the surgeon may employ the assistance of stapling, lasers and other modern surgical techniques with their attendant advantages.

Once the uterus and any adnexa are separated and any necessary adjunct procedures are completed, the retractor 10 may be employed to lift the uterus and any attached adnexa out of the abdominal cavity 110 through the incision 112. The hysterectomy procedure is then concluded in the conventional fashion. The entire procedure may be performed in 30 minutes or less as compared to the conventional abdominal hysterectomy procedures which typically require 60 minutes or more.

Although preferred embodiments of the present invention have been described in the foregoing detailed description, it will be understood that the invention is capable of numerous modifications, substitutions, alterations and replacements without departing from the scope and spirit of the following claims. For example, as shown in FIGS. 10 and 12, the retractor 10 may include as a further form of the handle means 18' a grip 120 dimensioned in general outline like the grip 50 described above with reference to FIGS. 2 through 6. The grip 120 is preferably a solid stainless steel casting with four finger holds 122 arranged along a front edge 124 extending the length of the grip. In this form of the retractor 10', a rod 22' is divided into two parts A and B along a separation line 126 that is oriented perpendicular to the length of the rod 22'. Part A contains a bend 46' and supports the engagement means 16 previously described above with respect to FIG. 1; and part B contains a bend 44' and supports the previously described piercing means 14, the line 126 being located close to the bend 44' so as to lie outside the uterus in the abdominal cavity when piercing means 14 is pierced through the fundus as described earlier. A blind bore 128 is formed in the end of part A and threadably receives a screw 130 provided on the end of part B, thereby providing for removal of part B from part A which occurs after piercing means 14 is pierced through the fundus of the uterus.

The grip 120 is provided with a screw 132 mounted on a boss 133, the screw 132 corresponding to screw 130 on part B and being located between the middle two finger holds 122. Once part B is removed from part A such as after piercing means 14 is pierced through the fundus of the uterus, attachment of the grip 120 to part A is accomplished by threading screw 132 into bore 128 provided in the end thereof. Thereafter, grip 120 may be used to apply forces to the engagement means 16 and thus the cervix as described above.

As a further feature, the retractor may include uterine retainer means for pressing the uterus against engagement means 16 to steady the uterus during the procedure. With reference to FIGS. 11 and 12, the uterine retainer means are preferably provided by a thin, rectangular member 142 (shown in FIG. 11) formed of a surgically compatible material such as stainless steel. A circular opening 144 is provided in the approximate center of the member 142 and has a diameter large enough to permit placement of member 142 onto the rod 22' by inserting the outer or free end of the rod into opening 142. Thus, the member 142 may be slipped onto rod 22' from the free end of part A after removal of part B and prior to attachment of the grip 120. The member 142 is selectively held at desired locations along the length of rod 22' by positioning the edge of the opening 144 down into a selected one of a plurality of longitudinally spaced-apart notches 146 (shown only on the rod 22' for the purpose of clarity but equally suitable for use on other forms of the shaft means 12 such as the rod 22 of FIG. 1). The notches 146 have a depth and configuration sufficient to hold the member 142 in opposition to a force exerted by the uterus which is engaged and compressed between the member 142 and the engagement means 16. Preferably, the notches 146 are located on the side of the rod 22' which will be in the "up" position once the retractor has been positioned to apply forces to the cervix as described earlier.

From the foregoing, therefore, it will be recognized that the embodiments and features of the retractor of the present invention which are shown and described herein are provided for the purpose of illustration only and that no undue limitations on the scope of the claims are to be construed as arising therefrom.

What is claimed is:

1. A uterine retractor for use in performing an abdominal hysterectomy involving removal of the uterus through an abdominal incision, the uterus having a cervix at one end connected to the vagina with a cervical canal through which access is gained to the interior space of the uterus from the vaginal canal, and a fundus closing the other end of the uterus and located in the abdominal cavity, said retractor comprising elongate shaft means having first and second opposite ends, piercing means located adjacent said first end of said shaft means for being guided into the interior space of the uterus through the cervical canal from the vaginal canal and configured to pierce through the fundus of the uterus to dispose said first end outside the uterus in the abdominal cavity, and engagement means located adjacent said second end for engaging the cervix and configured to engage the cervix and apply a force to the cervix to facilitate movement of the cervix to desired positions in response to application of a force on the retractor from said first end disposed outside the uterus in the abdominal cavity.

2. The retractor of claim 1, further comprising handle means attachable to said first end of said shaft means and configured to facilitate application of a force on the engagement means from said first end and thus facilitate movement of the cervix to desired positions as aforesaid.

3. The retractor of claim 1, wherein said shaft means comprises an elongate metal rod including an essentially straight section along a substantial portion of its length and having first and second opposite ends corresponding respectively to said first and second opposite ends of said shaft means, and said engagement means for engaging the cervix comprises a pessary cup fixedly connected to said second end of said rod and having a circumferentially extending outer lip lying in a plane which is disposed at an angle of less than about 30 degrees relative to the longitudinal axis of said straight section of said rod.

4. The retractor of claim 1, wherein said shaft means comprises an elongate smooth-surfaced rigid metal rod bent in generally opposite directions adjacent its first and second opposite ends at angles less than about 30°.

5. The retractor of claim 4, wherein said bends are such that the end portions of said rod extending outwardly from said bends extend along substantially parallel lines.

6. The retractor of claim 4, wherein two bends are provided, both being located from about one to about two inches from the adjacent end of the rod, and wherein the overall length of the rod is about 12 inches.

7. The retractor of claim 1, wherein the overall length of said shaft means between said first and second ends is about 12 inches.

8. The retractor of claim 1, wherein said shaft means comprises a rigid elongate rod having first and second opposite ends corresponding respectively to said first and second opposite ends of said shaft means, said piercing means comprises a forwardmost pointed tip for piercing through the fundus of the uterus, said point tapering forwardly from an elongate cylindrical portion defined integrally with said rod on said first end thereof, said cylindrical portion having a plurality of circumferentially spaced apart recesses disposed in a plane generally perpendicular to the length of said cylindrical portion, and the retractor further comprises handle means having engagement means releasably engageable into at least one of said recesses to interengage said handle means and said rod and thus facilitate the application of forces on said rod through application of forces to said handle means, and to enable rotation of said handle means relative to said rod between selected engaged positions.

9. A method of performing an abdominal hysterectomy involving removal of the uterus from the body through an abdominal incision, the uterus having a cervix at one end connected to the vagina with a cervical canal opening into the vaginal canal and through which access is gained to the interior space of the uterus from the vaginal canal, and a fundus closing the other end of the uterus and located in the abdominal cavity, the method comprising:

providing a uterine retractor comprising elongate shaft means having first and second opposite ends, piercing means located adJacent the first end for piercing through the fundus of the uterus to dispose the first end outside the uterus in the abdominal cavity, and engagement means located adjacent the second end for engaging and moving the cervix in response to a force applied to the retraction from the first end disposed outside the uterus in the abdominal cavity;

guiding the first end of the retractor and the piercing means located adjacent thereto into the interior space of the uterus from outside the body through the vaginal and cervical canals;

causing the piercing means to pierce through the fundus of the uterus so that the first end of the retractor projects out into the adjacent abdominal cavity;

applying a force to the projecting first end of the retractor to cause the engagement means thereof to engage and move the cervix to a desired position to facilitate separation of the uterus from adjacent attached body structure including the vagina;

separating the uterus from adjacent attached body structure while the uterus is positioned for separation as aforesaid;

uniting body structure and performing necessary procedures adjacent the area from which the uterus is removed to facilitate post-operative healing and promote resumption of normal body functions; and closing the abdominal incision.

10. The method of claim 9 further comprising employing the retractor to lift the separated uterus out of the abdominal cavity through the abdominal incision.

11. The method of claim 9, wherein the force is applied to the retractor by attaching a handle to the first end, gripping the handle, and applying force to the retractor through the gripped handle.

12. The method of claim 9, wherein the cervix is moved cranially by the retractor to stretch the vagina and thus facilitate separation of the uterus from the vagina.

* * * * *